United States Patent [19]
Nelson

[11] Patent Number: 5,773,016
[45] Date of Patent: Jun. 30, 1998

[54] INSECTICIDALLY-ACTIVE WATER-IN OIL-OUT EMULSIONS AND INSECTICIDALLY ACTIVE COMPOSITIONS DERIVED THEREFROM

[75] Inventor: Kurt D. Nelson, Mt. Pleasant, Wis.

[73] Assignee: S C. Johnson & Son, Inc., Racine, Wis.

[21] Appl. No.: 841,090

[22] Filed: Apr. 29, 1997

Related U.S. Application Data

[63] Continuation of Ser. No. 379,247, Jan. 27, 1995, abandoned.

[51] Int. Cl.$^6$ .................................................. A01N 25/06
[52] U.S. Cl. ................... 424/405; 424/45; 424/DIG. 10; 514/919; 514/938
[58] Field of Search ..................... 424/45, 405, DIG. 10; 514/937, 919, 938

[56] References Cited

U.S. PATENT DOCUMENTS

| | | | |
|---|---|---|---|
| 1,707,466 | 4/1929 | Volck | 424/405 |
| 2,017,506 | 10/1935 | Mills | 424/405 |
| 2,418,652 | 4/1947 | Maxwell | 424/45 |
| 3,092,555 | 6/1963 | Horn | 424/405 |
| 3,131,153 | 4/1964 | Klausner | 424/45 |
| 3,159,535 | 12/1964 | Sesso et al. | 424/45 |
| 3,303,091 | 2/1967 | Mailander et al. | 424/405 |
| 4,515,810 | 5/1985 | Chow et al. | 424/405 |
| 4,668,507 | 5/1987 | Tomkins et al. | 424/405 |
| 4,822,613 | 4/1989 | Rodero | 424/405 |
| 4,826,674 | 5/1989 | Albanese | 424/45 |
| 4,851,438 | 7/1989 | Flashinski | 514/531 |
| 4,889,710 | 12/1989 | Hagarty | 424/45 |
| 4,904,464 | 2/1990 | Albanese | 424/45 |
| 4,923,897 | 5/1990 | Flashinski | 514/531 |
| 5,094,853 | 3/1992 | Hagarty | 424/45 |
| 5,104,658 | 4/1992 | Hagarty | 424/45 |
| 5,116,618 | 5/1992 | Hagarty | 424/45 |
| 5,171,577 | 12/1992 | Griat et al. | 424/450 |
| 5,178,871 | 1/1993 | Thill | 424/405 |
| 5,346,699 | 9/1994 | Tiernan et al. | 424/405 |

FOREIGN PATENT DOCUMENTS

| | | |
|---|---|---|
| 0-069906 | 6/1984 | European Pat. Off. . |
| 93/00007 | 1/1993 | WIPO . |

OTHER PUBLICATIONS

Database WPI, Section Ch, Week 7707, Derwent Publications Ltd., London, GB, Abstract for JP, A, 52 001 031 (6 Jan. 1977).

*Primary Examiner*—Raj Bawa

[57] ABSTRACT

An insecticidally-active water-in oil-out emulsion of limited stability is disclosed. The emulsion contains at least water, a hydrocarbon solvent, an insecticidally active material, and a surfactant. When this emulsion is sprayed onto a target surface, an aqueous phase separates from an oil phase in the air or shortly after hitting a target surface.

12 Claims, No Drawings

5,773,016

INSECTICIDALLY-ACTIVE WATER-IN OIL-OUT EMULSIONS AND INSECTICIDALLY ACTIVE COMPOSITIONS DERIVED THEREFROM

BACKGROUND OF THE INVENTION

This is a continuation of application Ser. No. 08/379,247 filed Jan. 27, 1995, now abandoned.

FIELD OF THE INVENTION

The present invention relates to an insecticidally-active composition that forms an oil-out emulsion of limited stability. This composition when sprayed onto a target surface does not leave unsightly milky residues. Moreover, it is highly effective in killing insects.

DESCRIPTION OF THE BACKGROUND ART

Insecticidally-active compositions are generally sprayed from a container such as an aerosol container onto a target surface. For successful spraying that is uniform and evenly distributed, the composition must be homogeneous or nearly homogeneous. Traditionally, many insecticidally-active compositions have had a single homogeneous oil phase. However, such compositions usually have high flammability and contribute petroleum volatiles to the atmosphere.

To reduce the oil content, compositions were developed that form a stable homogeneous emulsion containing an aqueous phase and an oil phase, such as those disclosed in U.S. Pat. Nos. 3,159,535 and 3,303,091. U.S. Pat. No. 5,178,871 discloses a stable, double emulsion. However, when such compositions are sprayed onto a target surface, unsightly milky residues that characterize the appearance of an emulsion frequently are left on the surface, at least until the composition thoroughly dries.

Compositions have also been developed that form water-out (or oil-in-water) emulsions, in which the aqueous phase is the continuous phase and the oil phase is the embedded or discontinuous phase, such as those disclosed in U.S. Pat. No. 4,822,613, 4,889,710, 4,923,897, and 5,094,853. However, such compositions typically form a stable foam when they are sprayed onto a target surface. Moreover, if the active ingredient is dissolved or dispersed in the aqueous phase, the active ingredient does not penetrate water repelling chitin insect surfaces effectively.

U.S. Pat. No. 2,418,652 discloses a water-out emulsion to which a cationic emulsifier has been added, albeit in an amount less than an emulsifying amount. The cationic material is believed to adjust the surface charge of the suspended oil globules of the water-out emulsion to increase their ability to adhere to a generally negatively charged leaf surface.

U.S. Pat. No. 1,707,466 discloses a concentrated, stable oil emulsion that can be diluted with water to form a stable dispersion of oil in water. Although the dispersion is disclosed as stable over time while in its container, it is said to substantially break down upon contacting the target surface to coat plants or insect eggs with oil, combatting insect scale and killing the coated insect eggs. No insecticide is used other than the oil itself.

U.S. Pat. No. 4,904,464 discloses an insecticide composition containing cocodiethanolamide that separates into distinct water and oil phases, which, upon agitation, form an unstable dispersion, as opposed to an oil-out emulsion, that separates upon dispensing immediately subsequent to agitation.

SUMMARY OF THE INVENTION

The present inventors have discovered a novel insecticidally-active composition that does not leave unsightly milky stains when sprayed onto a target surface. The composition is also highly effective in killing a variety of insects, including roaches, ants, silverfish, crickets, and spiders.

In one embodiment, the present invention provides an insecticidally-active composition that forms an oil-out emulsion of limited stability, comprising:

an aqueous phase comprising water;

an oil phase comprising a hydrocarbon solvent and at least one active ingredient; and an amount of a surfactant effective to form a non-foaming oil-out emulsion of limited stability; whereby when the emulsion is first formed within and then sprayed from a container, the aqueous phase separates out at least partially from the oil phase in the air or upon hitting a target surface.

DETAILED DESCRIPTION OF THE INVENTION

The insecticidally-active composition of the present invention includes an aqueous phase and an oil phase. An insecticidally-active ingredient that is oil soluble and substantially water insoluble is dissolved in the oil phase.

The insecticidally-active composition of the invention forms an oil-out emulsion of limited stability. An emulsion made in accordance with the invention shall be considered to be of limited stability if it is visually apparent that it at least begins to separate within fifteen seconds of the cessation of brisk manual shaking in a bottle or other closed container.

An oil-out emulsion having oil and aqueous phases (or, as an equivalent term, a water-in-oil emulsion) is a type of emulsion in which the oil phase is the continuous phase and the aqueous phase is the embedded or discontinuous phase. Because the oil-out emulsion of this invention has limited stability, the aqueous phase and the oil phase of the composition usually separate during storage, at least partially.

When the two phases of the insecticidally-active composition of the invention are mixed together, for example, by shaking or agitating a container containing the composition, an oil-out emulsion is formed that is substantially foam-free but that also is homogeneous or nearly homogeneous. When this emulsion is sprayed from the container, the aqueous phase separates out from the oil phase at least partially and preferably completely, while the emulsion is still traveling through the air or promptly upon its hitting a target surface. Typically, the aqueous phase separates out within about 10 seconds after the emulsion is sprayed. Preferably, the aqueous phase separates out within about 5 seconds, and most preferably, the aqueous phase separates out immediately after the emulsion is sprayed. As a result, no unsightly milky residue that characterizes the appearance of an emulsion is left on the target surface.

Many insects have a exoskeleton made mainly of chitin, which has a water repellent surface. Water easily sheds from chitin surfaces without much penetration into the pores of the insect surfaces. In the present invention, the aqueous phase separates out from the oil phase and runs off, leaving the oil phase and its dissolved insecticidally-active ingredient on the insect surface. The oil phase wets the surface, with the result that the insecticidally-active ingredient carried in the oil phase more effectively penetrates the surface pores. Consequently, the composition of this invention is highly effective in killing insects.

Preferably a surfactant is present in the composition in an amount that is effective to provide an oil-out emulsion of limited stability. If the amount of the surfactant present is excessive, the emulsion may become too stable and take on an excessively milky appearance. That is, the aqueous phase and the oil phase will not separate sufficiently after spraying. If the amount of the surfactant present is insufficient, the composition may not form an emulsion, at all. Typically, the amount of surfactant present is from about 0.03% to about 0.10%, preferably from about 0.05% to about 0.10% by weight, based on the total weight of the composition.

Non-ionic, anionic, and cationic surfactants can all be used in the composition of this invention so long as the surfactant can cause the formation of an oil-out emulsion by manual shaking of the composition in a bottle or can. Preferably, the surfactant has a hydrophilic/lipophilic balance (hereafter referred to as an "HLB") of between about 3 and about 9. If the surfactant has an HLB greater than about 9, a water-out emulsion could form upon shaking, instead of an oil-out emulsion. If the surfactant has an HLB less than about 3, it becomes difficult to form an emulsion in-situ by shaking the container holding the composition.

Non-ionic surfactants are the preferred surfactants used in the composition of the present invention because they generally exhibit low toxicity to humans and non-target animals and are non-corrosive. Cationic surfactants tend to be corrosive to the commercially common metal containers typically used to contain insecticidal sprays. Anionic surfactants may cause nasal irritation if breathed and may also cause the formation of foam.

Examples of suitable non-ionic surfactants include long chain fatty acid esters of polyhydroxylic compounds such as glycol, glycerol, and sorbitol esters of oleic, stearic, palmitic, and lauric acids; polyethoxylated fatty alcohols having 2 to 9 ethylene oxide units; and polyethoxylated nonyl phenols having 2 to 9 ethylene oxide units.

The preferred non-ionic surfactants are sorbitan monooleate, sorbitan monostearate, and sorbitan monopalmitate, which are commercially available as Span®80, Span®60, and Span®40, respectively, from ICI Specialty Chemicals. The most preferred non-ionic surfactant for the composition of this invention is sorbitan monooleate.

The oil phase of the composition of this invention contains a hydrocarbon solvent. The amount of the solvent present in the composition should be effective to dissolve the active ingredient and form an oil-out emulsion. Typically, the hydrocarbon solvent is present in the composition in an amount of from about 0.5% to about 40% and preferably from about 5% to about 30% by weight, based on the total weight of the composition.

Examples of suitable hydrocarbon solvents include aliphatic, aromatic, and naphthenic solvents, and mixtures thereof. Examples of suitable aliphatic hydrocarbons include isoparaffinic and normal paraffinic solvents such as those commercially available from Exxon Chemicals of Houston, Tex. under the ISOPAR® and NORPAR® brand names. Examples of suitable aromatic solvents include benzene, toluene, and xylene. Examples of suitable naphthenic solvents include dearomatized aliphatics and isoparaffins containing naphthenic groups. Naphthenic solvents are usually commercially available as mixtures of naphthenic, normal paraffinic, and/or isoparaffinic solvents. Examples of suitable naphthenic solvents that are commercially available include EXXSOL® D-40, D-60, D-80, D-110, and D-130 from Exxon Chemicals, Houston, Tex. A preferred hydrocarbon solvent for use in the present invention is a mixture of naphthenic and normal paraffinic solvents, commercially available as EXXSOL® D-60.

A co-solvent that is soluble in both the aqueous phase and the oil phase may also be added to the composition of this invention. The co-solvent aids in the solubilization of the insecticidally active ingredient in the oil phase and also accelerates the breaking of the emulsion. Typically, the amount of the co-solvent present is from about 1% to about 5% by weight, based on the total weight of the composition. If the amount exceeds about 5%, an emulsion may not form. Examples of suitable co-solvents include alcohols such as methanol, ethanol, propanol, and isopropanol.

As disclosed, above, the composition of the present invention contains at least one insecticidally-active ingredient in an amount effective to provide insecticidal activity. Any conventional active ingredient that is water-insoluble and hydrocarbon solvent-soluble can be used. Examples of suitable active ingredients include but are not limited to natural pyrethrins, synthetic pyrethroids such as permethrin, cypermethrin, deltamethrin, alphamethrin, cyphenothrin, fenvolerate, allethrin, tetramethrin, resmethrin, bioresmethrin, d-trans-allethrin, and phenothrin, halogenated pyrethroids, and cyano-pyrethroids. Typically, the active ingredient is present in the composition of the present invention in an amount of from about 0.20% to about 2% and preferably from about 0.10% to about 1% by weight, based on the total weight of the composition. A synergist for the active ingredient may also be included in the composition of this invention in conventional amounts. Examples of suitable synergists include piperonyl butoxide and N-octyl bicycloheptene dicarboximide.

The water forming the aqueous phase of the composition of the invention should be present in an amount effective to form an oil-out emulsion of limited stability and to facilitate spraying. When the composition is sprayed from a container, the water functions as a filler to add bulk to the sprayed product. Typically, water is present in the composition in an amount of from about 30% to about 70% and preferably from about 40% to about 70% by weight, based on the total weight of the composition.

The insecticidally-active composition of the present invention may be combined with a suitable propellant to form an aerosol formulation. Examples of suitable propellants include compressed gas propellants such as nitrogen, carbon dioxide, and nitrous oxide; liquefied gas propellants such as fluorinated and chlorinated hydrocarbons, dimethyl ether, vinyl chloride; saturated hydrocarbons such as propane, butane, isobutane, isopentane, and mixtures thereof; and mixtures of liquefied gases and compressed gases. In order to reduce environmental pollution, it is preferred to employ as the propellant liquefied saturated hydrocarbons.

Typically, the hydrocarbon propellant is present in the composition of this invention in an amount of from about 8% to about 50% and preferably from about 5% to about 30% by weight, based on the total weight of the composition.

Other ingredients that may form a part of the composition of the present invention include fragrance in conventional amounts to mask the unpleasant odor of the active ingredients and corrosion inhibitors such as sodium nitrite, sodium benzoate, and mixtures thereof in conventional amounts to inhibit corrosion of the metal containers in which the composition is usually contained.

The present invention will now be illustrated with the following non-limiting Example.

EXAMPLE

An insecticidally-active composition that can form an oil-out emulsion of limited stability was prepared with the following ingredients.

| Ingredients | Percent By Weight |
|---|---|
| Pyrethrin 20% | 1.000 |
| Permethrin 90% | 0.222 |
| Piperonyl Butoxide | 0.500 |
| Sorbitan Monooleate | 0.050 |
| Fragrance | 0.228 |
| Isopropanol | 1.000 |
| EXXSOL ® D-60 | 29.000 |
| Sodium Nitrite | 0.090 |
| Water | 59.910 |
| Propellant A-91 | 8.000 |

Propellant A-91 is a conventional propellant containing 70% propane and 30% isobutane.

The composition was prepared by dissolving the pyrethrin 20%, permethrin 90%, piperonyl butoxide, sorbitan monooleate, fragrance, and isopropanol in EXXSOL® D-60 to form a solvent intermediate. The sodium nitrite was dissolved in water to form a water intermediate. The water intermediate was then added to an aerosol container, followed by the solvent intermediate. A valve was then placed into the container and crimped. The container was then pressurized with propellant A-91.

The container was then shaken to form an oil-out emulsion of limited stability. Promptly thereafter, the composition was sprayed from the container onto a target surface. It was observed that when the spray hit the target surface, the aqueous phase separated out from the oil phase almost immediately. As a result, no unsightly milky stains were left on the target surface.

While the present invention has been described with respect to what is presently considered to be the preferred embodiments, it is to be understood that the invention is not limited to the disclosed embodiments. On the contrary, the invention is intended to cover various modifications and equivalent formulations included within the spirit and scope of the appended claims. The scope of the following claims is to be accorded the broadest interpretation so as to encompass all such modifications and equivalent formulations and functions.

INDUSTRIAL APPLICABILITY

Sprayable insecticidal compositions have immediate usefulness in the control of insect pests. The insecticidally-active composition of the invention has the further industrially desirable application of providing a composition having reduced concentration of petroleum volatiles while still being both convenient for spraying by conventional means and an effective killer of insects sprayed.

We claim:

1. An insecticidally-active water-in oil-out emulsion that has been formed by mixing its components together, comprising:

30%–70% by weight water;

a hydrocarbon solvent that is not a gas propellant, that is present in an oil phase of the emulsion, that is selected from the group consisting of aliphatic, aromatic, and naphthenic solvents, and mixtures thereof, and that is 0.05%–40% by weight of the emulsion;

between 0.2% and 2% by weight of insecticidal active selected from the group consisting of natural pyrethrins, synthetic pyrethroids, halogenated pyrethroids, and cyano-pyrethroids; and an amount of surfactant effective to form a non-foaming water-in oil-out emulsion which upon visual inspection appears to completely separate into a composition with an oil phase and a water phase within fifteen seconds after said mixing of the emulsion has ceased, the surfactant being present in an amount of from 0.03% to 0.10% by weight, based on the total weight of the emulsion;

wherein the surfactant has an HLB of between about 3 and about 9 and is selected from the group consisting of glycol, glycerol, and sorbitol esters of oleic, stearic, palmitic, and lauric acids, polyethoxylated fatty alcohols having 2 to 9 ethylene oxide units, sorbitan, monooleate, sorbitan monostearate, and sorbitan monopalmitate and polyethoxylated nonyl phenols having 2 to 9 ethylene oxide units.

2. The insecticidally-active emulsion according to claim 1, wherein said surfactant is present in an amount of from about 0.05% to about 0.10%.

3. The insecticidally-active emulsion according to claim 1, wherein said emulsion further comprises a co-solvent.

4. The insecticidally-active emulsion according to claim 3, wherein said co-solvent is an alcohol.

5. The insecticidally-active emulsion according to claim 1, further comprising a synergist for said insecticidal active.

6. The insecticidally-active emulsion according to claim 5, wherein said synergist is selected from the group consisting of piperonyl butoxide and N-octyl bicycloheptene dicarboximide.

7. The insecticidally-active emulsion according to claim 1, further comprising a propellant.

8. The insecticidally-active emulsion according to claim 7, wherein said propellant is selected from the group consisting of liquefied saturated hydrocarbons and mixtures thereof.

9. The insecticidally-active emulsion according to claim 1, wherein said composition further comprises a fragrance.

10. The insecticidally-active emulsion according to claim 1, wherein said composition further comprises a corrosion inhibitor.

11. The insecticidally-active emulsion according to claim 10, wherein said corrosion inhibitor is selected from the group consisting of sodium nitrite, sodium benzoate, and mixtures thereof.

12. The composition of claim 1, wherein the composition was formed by separation of the claim 1 emulsion.

* * * * *

UNITED STATES PATENT AND TRADEMARK OFFICE
CERTIFICATE OF CORRECTION

| | |
|---|---|
| PATENT NO. | : 5,773,016 |
| APPLICATION NO. | : 08/841090 |
| DATED | : June 30, 1998 |
| INVENTOR(S) | : Kurt D. Nelson |

It is certified that error appears in the above-identified patent and that said Letters Patent is hereby corrected as shown below:

Column 6, Lines 23 and 24: replace "sorbitan, monooleate," with --sorbitan monooleate,--

Signed and Sealed this

Second Day of November, 2010

David J. Kappos
*Director of the United States Patent and Trademark Office*